(12) United States Patent
Kato et al.

(10) Patent No.: US 8,617,603 B2
(45) Date of Patent: *Dec. 31, 2013

(54) COATED TABLET

(75) Inventors: Hironobu Kato, Odawara (JP);
Hirokazu Sakamoto, Ichinomiya (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/607,395

(22) Filed: Sep. 7, 2012

(65) Prior Publication Data

US 2013/0004577 A1  Jan. 3, 2013

Related U.S. Application Data

(63) Continuation of application No. 12/304,015, filed as application No. PCT/JP2007/061777 on Jun. 12, 2007, now Pat. No. 8,282,956.

(30) Foreign Application Priority Data

Jun. 13, 2006  (JP) .................................. 2006-162972

(51) Int. Cl.
*A61K 9/28* (2006.01)
*A61K 9/20* (2006.01)

(52) U.S. Cl.
USPC ............................ 424/474; 424/464; 424/465

(58) Field of Classification Search
None
See application file for complete search history.

(56) References Cited

U.S. PATENT DOCUMENTS

| | | | |
|---|---|---|---|
| 5,891,474 A | 4/1999 | Busetti et al. | |
| 6,676,966 B1 | 1/2004 | Odidi et al. | |
| 2003/0166763 A1 | 9/2003 | Hoshi et al. | |
| 2005/0089571 A1 | 4/2005 | Beckert et al. | |
| 2005/0196418 A1 * | 9/2005 | Yu et al. | 424/401 |
| 2006/0134215 A1 | 6/2006 | Kondo et al. | |
| 2006/0229383 A1 | 10/2006 | Noami et al. | |
| 2010/0048641 A1 | 2/2010 | Nell et al. | |

FOREIGN PATENT DOCUMENTS

| | | |
|---|---|---|
| EP | 0431877 A1 | 6/1991 |
| EP | 1323404 | 7/2003 |
| EP | 1657265 A1 * | 5/2006 |
| JP | 4-145016 A | 5/1992 |
| WO | 00/25758 A1 | 5/2000 |
| WO | 02/17848 A1 | 3/2002 |
| WO | 2005/019286 A1 | 3/2005 |

OTHER PUBLICATIONS

Kowa Co., Ltd., Nikken Chemicals Co., Ltd., "Olmetec Tablets to Ensan Metformin Seizai matawa Mesilate Camostat Seizai tono Haigo Henka ni tsuite", [online], 2006 Nen 4 Gatsu, [retrieval date Jul. 26, 2007], Internet <URL: http://www.kowa-souyaku.co.jp/medical/product/index.htm>.

"Shinki Coating-zai PVA Copolymer no Kaihatsu", Fujii et al., Pharm Tech Japan, 2005, vol. 21, No. 2, pp. 67 (257)-71(261).

"Proceedings of the 22nd Synposium for Drug Formulation and Particle Design—Iyakuhintenkabutsu Polyvinyl alcohol—acrylic acid—methyl methacrylate Copolymer (PVA Copolymer) no kaihatsu" by KIDA et al., 2005, Hamamatsu, Japan, pp. 77-80.

International Search Report from PCT/JP2007/061777, dated Aug. 7, 2007.

* cited by examiner

*Primary Examiner* — Susan Tran
(74) *Attorney, Agent, or Firm* — McDermott Will & Emery LLP

(57) ABSTRACT

A main object of the present invention is to provide a novel coated tablet which contains a drug having a guanidino group and does not suffer an obvious color change even when packed in a one-dose pack together with a drug having a (5-methyl-2-oxo-1,3-dioxol-4-yl)methyl (DMDO) group. The present invention provides a coated tablet characterized in that an uncoated tablet containing a drug having a guanidino group has been coated with a polyvinyl alcohol for film coating which comprises polyvinyl alcohol, acrylic acid, and methyl methacrylate.

18 Claims, 1 Drawing Sheet

COATED TABLET

CROSS REFERENCE TO PRIOR APPLICATIONS

This patent application is a continuation application of U.S. patent application Ser. No. 12/304,015, filed on Jan. 13, 2009, which is a U.S. national phase application under 35 U.S.C. §371 of International Patent Application No. PCT/JP2007/061777, filed Jun. 12, 2007, and claims the benefit of Japanese Patent Application No. 2006-162972, filed Jun. 13, 2006. The International Application was published in Japanese on Dec. 21, 2007 as WO 2007/145191. The disclosures of all prior applications are hereby incorporated by reference in their entireties.

FIELD OF THE INVENTION

The present invention relates to a coated tablet which is coated with a polyvinyl alcohol copolymer for film coating.

BACKGROUND

For example, it is reported that, when a commercial metformin hydrochloride-containing tablet and a commercial olmesartan medoxomil-containing tablet are packed together in a one-dose pack, then the metformin hydrochloride-containing tablet turns reddish. This phenomenon is assumed to be caused by the event that the (5-methyl-2-oxo-1,3-dioxol-4-yl)methyl (hereinafter referred to as "DOMDO") group released from olmesartan medoxomil in the olmesartan medoxomil-containing tablet is hydrolyzed and converted into diacetyl and acetoin, and then these react with the guanidino group of metformin hydrochloride in the metformin hydrochloride-containing tablet. This reaction is known as Voges-Proskauel (VP) reaction. As a matter of course, however, the discoloration of drugs is unfavorable and it is considered necessary to prevent the discoloration by means of some devices in drug preparation methods.

In general, for the purpose of preventing or masking discoloration or coloration of medical and pharmaceutical tablets, uncoated tablets are coated. Depending on the properties of the compounds in uncoated tablets, the coating methods and coating agents are selected.

Recently, a polyvinyl alcohol copolymer for film-coating comprising polyvinyl alcohol (referred to hereinafter as "PVA"), acrylic acid and methyl methacrylate has been developed. This was first developed as a agent of capsules shell for solution-filling (see, for example, International Publication WO 02/17848); but owing to its excellent film formability, physical strength, adhesiveness, oxygen shieldability and the like, it has come to be applied as a film coating agent (POVA-COAT (trade name)) (see, for example, PHARM TECH JAPAN (2005) vol. 21, no. 2, pp. 257-261; Proceedings of the 22th Symposium for Drug Formulation and Particle Design, pp. 77-80 (2005 in Hamamatsu).

DISCLOSURE OF INVENTION

A main object of the present invention is to provide a novel coated tablet comprising a guanidino group-having drug, which does not exhibit obvious discoloration when packed together with a DMDO group-having drug in a one-dose pack.

The present inventors have intensively studied and found that the above object is achieved by a coated tablet in which an uncoated tablet containing guanidino group-having drug is coated with a PVA copolymer for film-coating (hereinafter simply referred to as "PVA copolymer") comprising PVA, acrylic acid and methyl methacrylate.

The present invention includes, for example:

(1) A coated tablet characterized in that an uncoated tablet containing a guanidino group-having drug is coated with a PVA copolymer comprising PVA, acrylic acid and methyl methacrylate.

(2) The coated tablet of the above (1), wherein the PVA, one constituent of the PVA copolymer has a degree of polymerization ranging from 400 to 600 and a degree of saponification ranging from 85 to 90 mol %.

(3) The coated tablet of the above (1) or (2), wherein the polymerization ratio of the constituents of the PVA copolymer is such that PVA is within a range of from 70 to 85% by weight; acrylic acid is within a range of from 2.0 to 8.0% by weight; and methyl methacrylate is within a range of from 17 to 21% by weight.

(4) The coated tablet of any one of the above (1) to (3), which is coated with the PVA copolymer within a range of from 0.5 to 20.0% by weight relative to the weight of the uncoated tablet.

5) The coated tablet of any one of the above (1) to (4), wherein the guanidino group-having drug is metformin hydrochloride, camostat mesilate, zanamivir hydrate, cetrorelix acetate, tegaserodmaleate, desmopressin acetate, eptifibatide, bivalirudin, ganirelix acetate, buserelin acetate, famotidine, triptorelin pamoate, pinacidil, histrelin, thymopentin, adrenochrome guanylhydrazone mesilate, cimetidine, benexate hydrochloride betadex, gusperimus hydrochloride, nafamostat mesilate, guanabenz acetate, or argatroban.

(6) A one-dose pack comprising at least the coated tablet of any one of the above (1) to (5) and a tablet that contains a drug having a (5-methyl-2-oxo-1,3-dioxol-4-yl)methyl (DMDO) group.

(7) The pack of the above (6), wherein the DMDO group-having drug is olmesartan medoxomil, prulifloxacin, or lenampicillin hydrochloride.

DETAILED DESCRIPTION OF THE INVENTION

Figure 1:
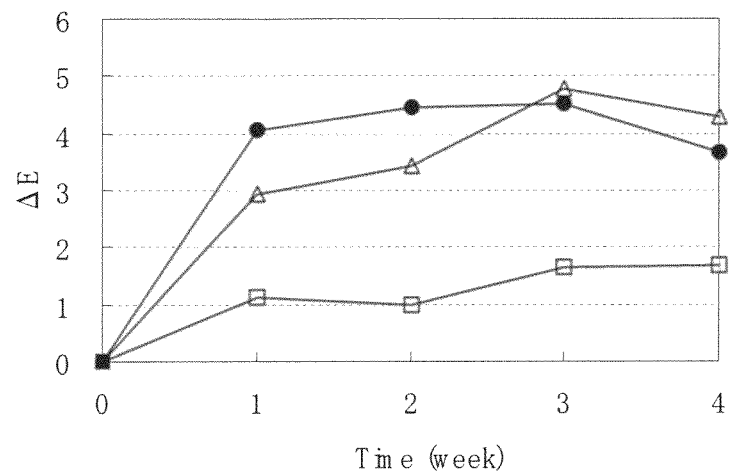
FIG. 1 Color change profile of tablets is shown. The vertical axis indicates color difference (ΔE), and the horizontal axis indicates time (week). In the drawing, -□- indicates the result of coated tablets of the present invention of Example 1; -Δ- indicates the result of hydroxypropylmethyl cellulose 2910-coated tablets of Comparative Example 1; and -●-indicates the result of Glycoran tablets (uncoated tablets).

The "PVA copolymer" used in the present invention is composed of PVA, acrylic acid and methyl methacrylic acid. The polymerization ratio of each constituent of the PVA copolymer is not particularly limited insofar as it can form a film as the PVA copolymer, and, for example, PVA is preferably within a range of from 70 to 85% by weight, acrylic acid is preferably within a range of from 2.0 to 8.0% by weight; and methyl methacrylate is preferably within a range of from 17 to 21% by weight. More preferably, PVA is within a range of from 75 to 80% by weight; acrylic acid is within a range of from 2.5 to 7.5% by weight; and methyl methacrylate is within a range of from 17.5 to 20% by weight.

The suitable "PVA" as one of the constituents of the PVA copolymer is such that the polymerization ratio is, for example, within the range of from 400 to 600, preferably within the range of from 450 to 550, and the degree of saponification is, for example, within the range of from 85 to 90 mol %, preferably within the range of from 86 to 89 mol %.

The PVA copolymer may be a commercial POVACOAT (registered mark, Nisshin-Kasei) in which PVA, acrylic acid and methyl methacrylate are copolymerised at a ratio of 80.0% by weight, 2.5% by weight and 17.5% by weight, respectively, and polymerization degree of the said PVA is 500 and saponification degree of the said PVA is within a range of from 86.5 to 89.0 mol % by weight.

The "guanidino group-having drug" contained in the coated tablet of the present invention refers to a drug having a guanidino group or a substituted guanidino group in the chemical structure of the drug. Herein, the substituted guanidino group refers to the guanidino group having the same or different 1 to 4 substituents at a substitutable position.

Examples of the substituents may include, for example, straight or branched alkyl, cyano, nitro, and pyridyl (e.g., 2-pyridyl, 3-pyridyl, 4-pyridyl).

Specific examples of the "guanidino group-having drug" may include metformin hydrochloride, camostat mesilate, zanamivir hydrate, cetrorelix acetate, tegaserod maleate, desmopressin acetate, eptifibatide, bivalirudin, ganirelix acetate, buserelin acetate, famotidine, triptorelin pamoate, pinacidil, histrelin, thymopentin, adrenochrome guanylhydrazone mesilate, cimetidine, benexate hydrochloride betadex, gusperimus hydrochloride, nafamostat mesilate, guanabenz acetate or argatroban.

The "DMDO group-having drug" refers to a drug having a DOMDO group in the chemical structure of the drug. Specific examples of the "DMDO group-having drug" may include olmesartan medoxomil, prulifloxacin or lenampicillin hydrochloride.

In the present invention, an uncoated tablet before being coated may be obtained by granulating an active ingredient such as guanidino group-having drug with an excipient, a disintegrant, a binder and so on and milling, followed by mixing the milled powder with a lubricant, and then compacting into a tablet. As for the excipient, the disintegrant, the binder and the lubricant, those materials which are commonly used for preparing tablets may be utilized.

The coated tablet of the present invention may be obtained by coating an uncoated tablet comprising a guanidino group-having drug with a coating solution containing a PVA copolymer by an ordinary method.

The content of the PVA copolymer in the coated tablet of the present invention is usually within a range of from 0.5 to 20% by weight relative to uncoated tablet weight, preferably within a range of from 1.0 to 10% by weight and more preferably within a range of from 1.5 to 5.0% by weight.

In addition, the content of the PVA copolymer in the coating layer may be usually within a range of from 40 to 80% by weight, preferably within a range of from 45 to 75% by weight and more preferably within a range of from 50 to 70% by weight.

An additive commonly used in the coating layer can be contained if necessary. The additive is not particularly limited insofar as it is a pharmaceutically acceptable additive, and, for example, coating agent (e. g., titanium dioxides, precipitated calcium carbonate), lubricant (e. g., talc), adsorbent (e. g., light anhydrous silicic acid, a hydrous silicon dioxide, magnesium silicate), colorant (e. g., red iron oxide, yellow iron oxide, titanium dioxide, tar dye) can be included. Among them, titanium dioxide is more preferable. For example, these additives can be included in an amount of less than 5% by weight in a coating solution together with a PVA copolymer, and can be involved in a coating layer through coating an uncoated tablet with the coating solution.

Hereinafter, the present invention is described in more detail by reference to the Examples, Comparative Examples and Test Examples. As a matter of course, the present invention is not limited to the following examples.

Example 1

Commercial Glycoran tablets (250 mg, uncoated tablets, by Nippon-Shinyaku) of a guanidino group-having drug were obtained; 10,800 g of the Glycoran tablets were put into an aeration drying-type coating machine (DRC-650 type, by Powrex); using a coating solution prepared by dissolving or suspending 400 g of a PVA copolymer (POVACOAT (registered trademark), by Nisshin Kasei), 264 g of titanium dioxide (TIPAQUE A-100, by Ishihara Sangyo) and 136 g of talc (Talc PKP-81, by Fuji Talc Industrial Co.) in 7,200 g of purified water, coated tablets of the present invention coated with the PVA copolymer in a ratio of 3.7% (w/w) relative to the weight of the uncoated tablet were obtained.

Comparative Example 1

Commercial Glycoran tablets (250 mg, uncoated tablets, by Nippon-Shinyaku) were obtained; 10,800 g of the Glycoran tablets were put into an aeration drying-type coating machine (DRC-650 type, by Powrex); using a coating solution prepared by dissolving or suspending 435.2 g of hydroxy propylmethyl cellulose 2910, 89.6 g of propylene glycol and 115.2 g of titanium dioxide (TIPAQUE A-100, by Ishihara Sangyo) in 5,760 g of purified water, comparative coated tablets coated with the hydroxy propylmethyl cellulose 2910 in a ratio of 4.0% (w/w) relative to the weight of the uncoated tablet, were obtained.

Comparative Example 2

Using a coating agent characterized by oxygen permeation shieldability like POVACOAT, pullulan (by Hayashibara), comparative coated tablets were produced.

Text Example 1

Commercial Glycoran tablets (250 mg, uncoated tablets; by Nippon-Shinyaku) were obtained; 10,800 g of the Glycoran tablets were put into an aeration drying-type coating machine (DRC-650 type, by Powrex); using a coating solution prepared by dissolving 400 g of pullulan (by Hayashibara) in 4,600 g of pure water, comparative coated tablets coated with the pullulan in a ratio of 3.7% (w/w) relative to the weight of the uncoated tablet were obtained.

Commercial Glycoran tablets (uncoated tablets), coated tablets produced in Example 1 and Comparative Example 1, three tablets, each were respectively put into a recloseable polyethylene bag (Unipack A-4, by Seisannippon) together with three tablets of a DMDO group-having drug Olmetec (20 mg, by Daiichi-Sankyo), and stored under the conditions of 40.degree. C. and 75% RH. After 1, 2, 3 and 4 weeks, the tablets were checked for discoloration with a color difference meter (spectral color difference meter SE2000, by Nippon Denshoku Kogyo).

The results are shown in FIG. 1. When the color difference (ΔE) is 3 or above, the reddish discoloration of the tablet is recognized with the naked eye; but significant color change could not be discernible with the naked eye when the value is not more than 2.5. The color difference (ΔE) means the numerical value converted from the data of color difference between the aged tablets and the original tablets before the test.

As is obvious from FIG. 1, the coated tablets of the present invention produced in Example 1 were remarkably prevented from being discolored, as compared with the Glycoran tablets and the hydroxypropylmethyl cellulose 2910-coated tablets produced in Comparative Example 1.

Text Example 2

Commercial Glycoran tablets (uncoated tablets), coated tablets produced in Example 1 and Comparative Example 2, three tablets, each were respectively packed with cellophan-poly (by Nihonshokai) together with three tablets of a DMDO group-having drug Olmetec (20 mg, by Daiichi-Sankyo), and stored under the conditions of 40.degree. C. and 75% RH. After 1 and 2 weeks, the tablets were checked for discoloration with a color difference meter (spectral color difference meter, SE2000, by Nippon Denshoku Kogyo).

Figure 2:
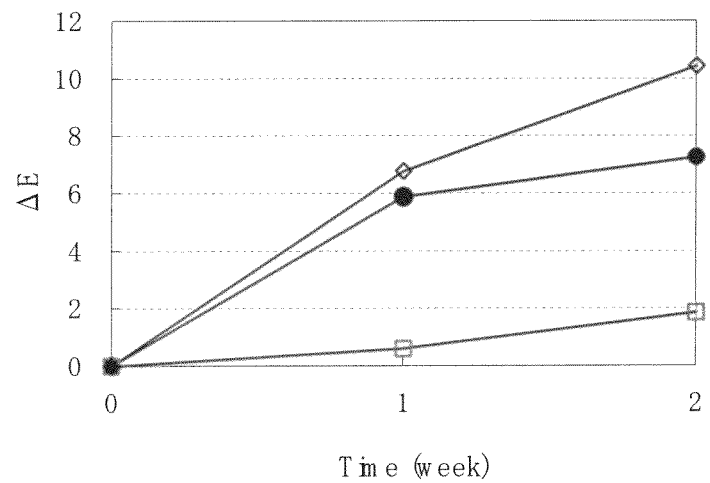
FIG. 2 Color change profile of tablets is shown. The vertical axis indicates color difference (ΔE), and the horizontal axis indicates time (week). In the drawing, -□- indicates the result of coated tablets of the invention of Example 1; -◇- indicates the result of PULLULAN (★)-coated tablets of Comparative Example 2; and -●- indicates the result of Glycoran tablets (uncoated tablets).

The results are shown in FIG. 2. When the color difference (ΔE) is 3 or above, the reddish discoloration of the tablet is recognized with the naked eye; but any clear color change could not be discernible with the naked eye when the value is not more than 2.5.

As is obvious from FIG. 2, the coated tablets of the present invention produced in Example 1 were remarkably prevented from being discolored, as compared with the Glycoran tablets produced in Comparative Example 2.

INDUSTRIAL APPLICABILITY

As described above, the coated tablet of the present invention can markedly prevent reddish discoloration reaction that could occur when the tablet was kept in contact with or in close contact with a DMDO group-having drug. Accordingly, the coated tablet of the present invention is useful since the color change of the tablet can be prevented even when packed in a one-dose pack together with a DMDO group-having drug.

The invention claimed is:

1. A method for preventing discoloration of a tablet containing a guanidino group-having drug due to close proximity with a tablet comprising a (5-methyl-2-oxo-1,3-dioxo1-4-yl) methyl (DMDO) group-having drug, said method comprises:
   providing a one-dose pack comprising:
      a coated tablet prepared by coating an uncoated tablet containing a guanidino group-having drug, with a polyvinyl alcohol copolymer for film-coating comprises polyvinyl alcohol, acrylic acid and methyl methacrylate; and
      a tablet comprising a drug having a (5-methyl-2-oxo-1,3-dioxol1-4-yl)methyl (DMDO) group-having drug.

2. The method of claim 1, wherein polyvinyl alcohol in the polyvinyl alcohol copolymer has a polymerization degree of from 400 to 600.

3. The method of claim 1, wherein the polyvinyl alcohol in the polyvinyl alcohol copolymer has a saponification degree of from 85 to 90 mol %.

4. The method of claim 1, wherein polymerization ratio of constituents of the polyvinyl alcohol copolymer for film-coating is such that the polyvinyl alcohol is within a range of from 70 to 85% by weight.

5. The method of claim 4, wherein the polyvinyl alcohol is within a range of from 75 to 80% by weight.

6. The method of claim 1, wherein polymerization ratio of constituents of the polyvinyl alcohol copolymer for film-coating is such that the acrylic acid is within a range of from 2.0 to 8.0% by weight.

7. The method of claim 6, wherein the acrylic acid is within a range of from 2.5 to 7.5% by weight.

8. The method of claim 1, wherein polymerization ratio of constituents of the polyvinyl alcohol copolymer for film-coating is such that the methyl methacrylate is within a range of from 17 to 21% by weight.

9. The method of claim 1, wherein the methyl methacrylate is within a range of from 17.5 to 20% by weight.

10. The method of claim 1, wherein polymerization ratio of constituents of polyvinyl alcohol copolymer for film-coating is such that the polyvinyl alcohol is within a range of from 70 to 85% by weight; the acrylic acid is within a range of from 2.0 to 8.0% by weight; and the methyl methacrylate is within a range of from 17 to 21% by weight.

11. The method of claim 1, wherein the polyvinyl alcohol copolymer is such that the polyvinyl alcohol, the acrylic acid and the methyl methacrylate are copolymerised at a ratio of 80.0% by weight, 2.5% by weight and 17.5% by weight, respectively, and polymerization degree of polyvinyl alcohol is 500 and the saponification degree of polyvinyl alcohol is within a range of from 86.5 to 89.0 mol % by weight.

12. The method of claim 1, wherein the weight of the coating is within a range of from 0.5 to 20.0% relative to the weight of the uncoated tablet.

13. The method of claim 12, wherein the weight of the coating is within a range of from 1 to 10.0% relative to the weight of the uncoated tablet.

14. The method of claim 1, wherein the weight of the coating is within a range of from 1.5 to 5.0% relative to the weight of the uncoated tablet.

15. The method of claim 1, wherein the guanidino group of the drug has 1 to 4 substituents.

16. The method of claim 15, wherein the substituents are selected from the group consisting of straight or branched alkyl, cyano, nitro, and pyridyl.

17. The method of claim 1, wherein the guanidino group-having drug is selected from the group consisting of metformin hydrochloride, camostat mesilate, zanamivir hydrate, cetrorelix acetate, tegaserod maleate, desmopressin acetate, eptifibatide, bivalirudin, ganirelix acetate, buserelin acetate, famotidine, triptorelin pamoate, pinacidil, histrelin, thymopentin, adrenochrome guanylhydrazone mesilate, cimetidine, benexate hydrochloride betadex, gusperimus hydrochloride, nafamostat mesilate, guanabenz acetate and argatroban.

18. The method of claim 1, wherein the DMDO group-having drug is selected from the group consisting of olmesartan medoxomil, prulifloxacin and lenampicillin hydrochloride.

* * * * *